United States Patent
Kidane (10) Patent No.: US 8,709,476 B2
(45) Date of Patent: Apr. 29, 2014

(54) COMPOSITIONS OF QUATERNARY AMMONIUM COMPOUNDS CONTAINING BIOAVAILABILITY ENHANCERS

(75) Inventor: Argaw Kidane, Montgomery Village, MD (US)

(73) Assignee: Supernus Pharmaceuticals, Inc., Rockville, MD (US)

(*) Notice: Subject to any disclaimer, the term of this patent is extended or adjusted under 35 U.S.C. 154(b) by 1580 days.

(21) Appl. No.: 10/980,819

(22) Filed: Nov. 4, 2004

(65) Prior Publication Data

US 2005/0123606 A1 Jun. 9, 2005

Related U.S. Application Data

(60) Provisional application No. 60/517,196, filed on Nov. 4, 2003.

(51) Int. Cl.
*A61K 9/20* (2006.01)

(52) U.S. Cl.
USPC .......................................................... 424/465

(58) Field of Classification Search
USPC .......................................................... 424/465
See application file for complete search history.

(56) References Cited

U.S. PATENT DOCUMENTS

| | | | |
|---|---|---|---|
| 2,095,282 A | 10/1937 | Payne | |
| 2,956,926 A * | 10/1960 | Greif | 424/452 |
| 3,065,143 A | 11/1962 | Christenson | |
| 4,259,314 A | 3/1981 | Lowey | |
| 4,556,552 A | 12/1985 | Porter et al. | |
| 4,650,664 A | 3/1987 | Schepky et al. | |
| 4,668,684 A | 5/1987 | Tibes et al. | |
| 4,713,243 A | 12/1987 | Schiraldi et al. | |
| 4,828,836 A | 5/1989 | Elger et al. | |
| 4,871,548 A | 10/1989 | Edgren et al. | |
| 4,940,588 A | 7/1990 | Sparks et al. | |
| 4,970,081 A | 11/1990 | Frisbee | |
| 5,158,777 A | 10/1992 | Abramowitz et al. | |
| 5,203,203 A | 4/1993 | Bryan et al. | |
| 5,242,927 A * | 9/1993 | Baker et al. | 514/299 |
| 5,273,760 A | 12/1993 | Oshlack | |
| 5,279,660 A | 1/1994 | Carlsson et al. | |
| 5,330,766 A | 7/1994 | Morella et al. | |
| 5,399,359 A | 3/1995 | Baichwal | |
| 5,405,648 A | 4/1995 | Hermann | |
| 5,455,047 A | 10/1995 | Bequette et al. | |
| 5,520,932 A | 5/1996 | McCurdy et al. | |
| 5,582,838 A * | 12/1996 | Rork et al. | 424/472 |
| 5,641,536 A | 6/1997 | Lech et al. | |
| 5,656,286 A | 8/1997 | Miranda et al. | |

(Continued)

FOREIGN PATENT DOCUMENTS

| | | |
|---|---|---|
| CA | 2 035 155 | 10/1991 |
| DE | 1 194 422 | 6/1965 |

(Continued)

OTHER PUBLICATIONS

Langguth et al (Euro Journal of Pharmaceutics and bippharmaceutics 43 (1997) 265-272).*

*Primary Examiner* — Benjamin Packard (74) *Attorney, Agent, or Firm* — Millen, White, Zelano & Branigan, P.C.

(57) ABSTRACT

An oral pharmaceutical dosage form with enhanced gastrointestinal permeability, comprising a therapeutic quaternary ammonium compound together with an organic acid.

30 Claims, 4 Drawing Sheets

(56) References Cited

U.S. PATENT DOCUMENTS

| | | | |
|---|---|---|---|
| 5,686,094 A | 11/1997 | Acharya | |
| 5,779,661 A | 7/1998 | Stephen et al. | |
| 5,837,285 A | 11/1998 | Nakamichi et al. | |
| 5,912,013 A | 6/1999 | Rudnic et al. | |
| 5,959,196 A | 9/1999 | Norcross | |
| 5,962,024 A | 10/1999 | Marvola | |
| 5,972,389 A | 10/1999 | Shell et al. | |
| 5,998,430 A | 12/1999 | Schwantes et al. | |
| 6,004,582 A | 12/1999 | Faour et al. | |
| 6,024,976 A | 2/2000 | Miranda et al. | |
| 6,063,808 A | 5/2000 | Fabiano | |
| 6,077,533 A | 6/2000 | Oshlack et al. | |
| 6,124,355 A | 9/2000 | Guittard et al. | |
| 6,141,625 A | 10/2000 | Smith et al. | |
| 6,156,340 A | 12/2000 | Adeyeye | |
| 6,197,331 B1 | 3/2001 | Lerner et al. | |
| 6,267,990 B1 | 7/2001 | Fischer et al. | |
| 6,312,726 B1 | 11/2001 | Nakamichi et al. | |
| 6,337,091 B1 | 1/2002 | Kim et al. | |
| 6,350,471 B1 | 2/2002 | Seth | |
| 6,375,985 B1 | 4/2002 | Bomberger et al. | |
| 6,437,000 B1 | 8/2002 | Mulye | |
| 6,534,091 B1 | 3/2003 | Garces et al. | |
| 6,569,462 B1 | 5/2003 | Cornelli | |
| 6,632,451 B2 | 10/2003 | Penhasi et al. | |
| 6,635,680 B2 | 10/2003 | Mulye | |
| 6,638,528 B1 | 10/2003 | Kanios | |
| 6,645,528 B1 | 11/2003 | Straub et al. | |
| 6,652,837 B1 | 11/2003 | Edwards et al. | |
| 6,682,759 B2 | 1/2004 | Lim et al. | |
| 6,772,801 B1 | 8/2004 | Shojaei et al. | |
| 6,897,205 B2 | 5/2005 | Beckert et al. | |
| 6,905,709 B2 | 6/2005 | Oshlack | |
| 6,923,988 B2 | 8/2005 | Patel et al. | |
| 6,962,717 B1 | 11/2005 | Huber et al. | |
| 6,974,820 B2 * | 12/2005 | Aberg | 514/278 |
| 7,410,978 B2 | 8/2008 | Kidane et al. | |
| 7,720,430 B2 | 5/2010 | Hasegawa et al. | |
| 2002/0031550 A1 | 3/2002 | Sauer | |
| 2002/0047058 A1 | 4/2002 | Verhoff et al. | |
| 2002/0091099 A1 | 7/2002 | Blackburn et al. | |
| 2002/0110593 A1 | 8/2002 | Penhasi et al. | |
| 2003/0012815 A1 * | 1/2003 | Ishibashi et al. | 424/471 |
| 2003/0054032 A1 | 3/2003 | Oshlack | |
| 2003/0054041 A1 | 3/2003 | Lemmens et al. | |
| 2003/0064108 A1 | 4/2003 | Lukas | |
| 2003/0147952 A1 | 8/2003 | Lim et al. | |
| 2003/0152627 A1 | 8/2003 | Beckert et al. | |
| 2003/0158176 A1 | 8/2003 | Richards et al. | |
| 2003/0185882 A1 | 10/2003 | Vergez et al. | |
| 2003/0199480 A1 | 10/2003 | Hayes | |
| 2004/0028729 A1 | 2/2004 | Shojaei | |
| 2004/0086571 A1 | 5/2004 | Guivarc'h et al. | |
| 2004/0091543 A1 | 5/2004 | Bell et al. | |
| 2004/0142035 A1 | 7/2004 | Chang | |
| 2004/0202693 A1 | 10/2004 | Chang | |
| 2004/0228917 A1 | 11/2004 | Oshlack | |
| 2005/0009862 A1 | 1/2005 | Sabounjian | |
| 2005/0043342 A1 | 2/2005 | Aberg | |
| 2006/0047007 A1 | 3/2006 | Danehower | |

FOREIGN PATENT DOCUMENTS

| | | |
|---|---|---|
| EP | 1 101 490 | 5/2001 |
| EP | 1 125 586 | 8/2001 |
| GB | 1 058 542 | 2/1967 |
| WO | WO-93 00991 | 1/1993 |
| WO | WO-95 05809 | 3/1995 |
| WO | WO-00 12069 | 3/2000 |
| WO | WO-00 27364 | 5/2000 |
| WO | WO-01 15668 | 3/2001 |
| WO | WO-01 54671 | 8/2001 |
| WO | WO-01 62236 | 8/2001 |
| WO | WO 0154671 A1 * | 8/2001 |
| WO | WO-02 060415 | 8/2002 |
| WO | WO-03 066028 | 8/2003 |
| WO | WO-2004 000280 | 12/2003 |
| WO | WO-2004 062577 | 7/2004 |
| WO | WO-2004 096125 | 11/2004 |

* cited by examiner

COMPOSITIONS OF QUATERNARY AMMONIUM COMPOUNDS CONTAINING BIOAVAILABILITY ENHANCERS

FIELD OF THE INVENTION

The present invention is directed to compositions of quaternary ammonium compounds containing bioavailability enhancers.

BACKGROUND OF THE INVENTION

The relatively poor absorption of quaternary ammonium compounds from the lumen of the gastrointestinal tract, in effect, limits their utility in therapy. It is often required that a higher dose be given or alternative routes of administration sought. Of course, higher doses are almost always associated with undesirable side effects.

Trospium chloride is a quaternary ammonium compound that was introduced in to the market as a spasmolytic agent in 1967 (German patent 1 194 422). This active agent has been available as an orally administrable, solid administration form (tablets and dragees), for intravenous or intramuscular injection as an injection solution, and for rectal administration as suppositories, and is mainly used for the treatment of bladder dysfunctions (urge incontinence, detrusorhyperreflexia). Due to its permanent positive charge, and hence low permeability, its bioavailability is extremely low (only up to 10% in humans). The oral dosage form is given in a fairly high dose and thus is associated with the typical side effects for anticholinergics, such as heart rate increases, dryness of the mouth, accommodation difficulties, etc.

There have been various attempts to enhance the permeability and bioavailability of poorly absorbed drugs. Cavallito et al (U.S. Pat. No. 2,899,357) used pharmacologically inactive quaternary ammonium compounds to enhance the absorption of pharmacologically active quaternary ammonium compounds. The theory behind their invention is based on the following principle: absorption of quaternary ammonium compounds in the gastrointestinal tract appears to be low because such compounds bind tightly to anionic receptors in the wall of the tract and hence are not readily available for absorption. For example, mucin is composed chiefly of polysaccharides with acidic functional groups that retain quaternary ammonium compounds by ionic interaction. By using other pharmacologically inactive compounds, Cavallito thought it was possible to saturate these binding sites, thereby leaving fewer sites for the pharmacologically active compound to bind to. The problem with this approach is that many of the quaternary ammonium compounds that are available are pharmacologically active, not inactive. Also, a high level of an inactive quaternary ammonium salt is needed for it to be effective.

Schepky et al (U.S. Pat. No. 4,650,664) used organic acids and their derivatives to enhance the solubility of drugs such as mopidamol that are poorly soluble in basic media. Such acids, by lowering the pH of the microenvironment, improve the solubility of basic drugs. Mechanistically, this approach is not suitable for quaternary ammonium or otherwise permanently charged molecules, as they are highly soluble in aqueous media irrespective of the pH of the media. Stern et al (U.S. Pat. No. 6,086,918) disclosed a formula that enhances the absorption of peptides by protecting the peptides from the acid environment of the stomach and at the same time lowering the pH of the intestinal fluid and hence providing an environment that is less favorable to the activity of proteolytic enzymes. They used organic acids such as citric and tartaric acids as pH lowering agents in the small intestine.

Other approaches to enhance the bioavailability of poorly permeable drugs include the use of vasodilators such as nicotinic acid (U.S. Pat. No. 5,126,348), the use of polyglycerol esters of unsaturated fatty acids to enhance the solubility of actives (U.S. Pat. No. 4,650,664), the use of carnithine derivatives and cyclodextrins (EPO 119737), the use of complex carbohydrates to enhance the absorption of calcium and other minerals (U.S. Pat. No. 4,689,228), the use of surface active agents to enhance the bioavailability of drugs (U.S. Pat. Nos. 4,571,334, 4,334,934, and EPO 031603), and the pro-drug approach (U.S. Pat. Nos. 4,673,534, 4,443,435, 4,694,006, and EPO 036534).

There still remains an unmet need in the art to enhance the bioavailability of therapeutic quaternary ammonium compounds.

SUMMARY OF THE INVENTION

It is the object of this invention to enhance the bioavailability of permanently charged molecules such as quaternary ammonium compounds by enhancing their permeability.

In this invention, this is achieved through the use of organic acids of various chain lengths. It was found that short chain organic acids are more effective than long chain organic acids.

In a further aspect, the present invention is directed to combining organic acids with polymers that will form complexes with quaternary ammonium compounds. These polymers are ones that will form complexes with the positively charged therapeutic molecules due to the presence of electronegative functional groups in their structure (for example, polyvinylpyrollidone) or negative charges (for example, sodium carboxymethylcellulose). These polymers in conjunction with organic acids synergistically enhance the permeability of quaternary ammonium compounds.

While not being bound to any particular theory, it is believed that polymers with electronegative or negatively charged functional groups enter into ionic (charge-charge) or ion-dipole type complex formations that fully or partially neutralize the positive charge of the quaternary ammonium compounds.

Polymers that form complexes and have electronegative atoms include all cellulosic polymers, alginates, gums such as guar and xanthan gums, polyacrylic acid derivatives such as carbomers, carageenan, povidone and its derivatives such as crospovidone, polyethylene oxides, and polyvinylalcohol. Examples of cellulosic polymers that are suitable for the formulations of the present invention include: hydroxypropylmethylcellulose (HPMC), hydroxypropylcellulose (HPC), hydroxyethylcellulose (HEC), methylcellulose (MC), powdered cellulose, cellulose acetate, sodium carboxymethylcellulose, calcium salt of carboxymethylcellulose, and ethylcellulose. Preferred are the cellulosic compounds, and most preferred is HPMC. The present formulations can use one or more of such polymers in the enhancer-containing compositions.

While the charge neutralization of the therapeutic agent by such polymer(s) is desirable and preferred in the present invention, it is not sufficient or conducive in itself to enhance the absorption of positively charged, quaternary ammonium compounds. In itself, the complex will have no better permeability than the free quaternary ammonium compound.

Organic acids function by opening up cell-to-cell tight junctions, thereby allowing molecules to diffuse through. When complex forming polymers are used in conjunction with tight junction opening molecules, however, the charge neutralization as well as tight junction opening occur simultaneously, resulting in a synergistic enhancing of the permeability of the quaternary ammonium compounds.

DETAILED DESCRIPTION OF THE INVENTION

This invention provides permeability/bioavailability enhancement for pharmacologically active quaternary ammonium or otherwise permanently charged molecules with limited permeability/bioavailability. Permeability through the epithelial layer of the gastro-intestinal tract (also known as the gut) is an important step in drug absorption. Other steps include, permeation through the mucosal layer that lines the gut surface, metabolism in the gut lumen as well as the gut wall. Bioavailability is qualitatively defined as the availability of drugs in the physiological system. For drugs such as quaternary ammonium compounds, the most important step in the process of drug absorption is the permeation of the drug through the epithelial barrier. Hence enhancing permeability of such drugs translates directly into increasing their bioavailability.

Permeability/bioavailability enhancement leads to lowering the dose hence reducing the unwanted side effects associated with high doses. It also compensates for the loss in bioavailability associated with extended release preparations for drugs with narrow window of absorption in the GI tract.

In this invention, permeability/bioavailability-enhanced compositions are formulated in such a way that the permeability/bioavailability enhancing excipients are released at the same time and in the same microenvironment with the drug. Synchronized release of the drug with a permeability enhancer is achieved through either coating the drug and permeability enhancing excipient with pH dependent enteric polymers, which can be the same or different as long as they will dissolve at the same or similar pHs, or by including compounds, such as electronegatively charged polymers, which enter in to a complex formation that partially or wholly neutralizes the charges on the drug molecules. This synchronized release is most preferably for the optimum performance of the permeability enhancers in the dosage forms of the present invention.

There are conceivably a number of dosage forms of the compositions contemplated by the present invention that will achieve the synchronized release of the drug and the permeability enhancer.

As an example of a preferred embodiment, the dosage unit can take the form of a granular permeability enhancing agent, which is surrounded by a layer of the quaternary ammonium active agent (with or without polymers that will form complexes with the active agent), and a layer of enteric or non-enteric polymer surrounding the drug layered enhancing agent. More particularly, granular forms of the permeability enhancing excipient (such as citric acid granules) are available from commercial suppliers. The particle size range for the commercially available excipients can vary; however, for the purposes of the present invention, granular excipients in a particle size range of 150 μm to 800 μm may be used, and preferably the size range is 300 μm to 700 μm. The most preferred particle size range for this application is 400 μm to 600 μm. In a preferred aspect, the excipient granules can be coated with a protective polymer Polymers that can be used to provide a protective layer include hydroxypropylemethylcellulose, hydroxyproylcellulose, ethylcellulose, hydroxyethylcellulose, Eudragit®L30D55, Eudragit®FS30D, Eudragit®RS, Eudragit®RL. The coating weight gain of this protective polymer can vary from 1% by weight to 10% by weight, preferably 2% to 5% by weight, and most preferably 5% by weight.

The polymer granules (coated or uncoated) are then layered with a solution containing the active drug, and optionally one or more polymers that will form complexes with the drug. The concentration of the drug in this layering solution can vary from 10% by weight to 50% by weight, depending on the desired drug load or the desired processing parameters. The preferred drug concentration in the coating solution is 30% by weight to 40% by weight.

Drug coated granules are then optionally coated with enteric or non-enteric polymers to achieve customized release profiles of both the drug and the permeability enhancing excipient.

Examples of enteric polymer coatings include, but are not limited to, cellulose acetate phthalate, cellulose acetate trimellitate, hydroxypropyl methylcellulose phthalate, polyvinyl acetate phthalate, carboxymethylethylcellulose, and co-polymerized methacrylic acid/methacrylic acid methyl esters such as, for instance, materials known under the trade name EUDRAGIT®L12.5, L100, or EUDRAGIT®S12.5, S100 or the like. Aqueous colloidal polymer dispersions or re-dispersions can also be used as enteric coatings, which include, e.g., EUDRAGIT®L 30D-55, EUDRAGIT®L100-55, EUDRAGIT®S100, EUDRAGIT®preparation 4110D (Rohm Pharma); AQUATERIC®, AQUACOAT® CPD 30 (FMC), KOLLICOAT MAE®30D and 30DP (BASF), and EASTACRYL®30D (Eastman Chemical).

Non-enteric polymers useful in achieving sustained release include, for example, cellulose acetate, cellulose acetate butyrate, cellulose acetate propionate, ethyl cellulose, fatty acids and their esters, waxes, zein, and aqueous polymer dispersions such as EUDRAGIT® RS and RL 30D, EUDRAGIT®NE 30D, AQUACOAT®, and SURELEASE®. A combination of the above polymers with hydrophilic polymers such as hydroxyethyl cellulose, hydroxypropyl cellulose (such as KLUCEL®, Hercules Corp.), hydroxypropyl methylcellulose (such as METHOCEL® Dow Chemical Corp.) can also be used. The combination allows for tailoring release profiles to those desired.

In another preferred embodiment, the permeability enhancing excipients are contained in coated granules, and drug layered spheres are contained in separate pellets. In this embodiment, granular permeability enhancing excipients are obtained from a commercial supplier of a particular size range, as, set forth above, or can be screened to achieve a desired size distribution. These excipient granules are then coated with either enteric or non-enteric polymer(s), as are set forth above. Drug containing (active) pellets are prepared separately by layering of a solution of the drug (with or without one or more polymers that will form complexes with the drug) onto nonpareil seeds (for example, sugar spheres). The active pellets are then coated with either the enteric or non-enteric polymer(s). Coated active pellets and coated permeability enhancing excipients are then filled into capsules of appropriate size or compressed into tablets.

In yet another preferred embodiment, a composition containing the active agent and permeability enhancer(s), with or without polymers that will complex with the drug, and preferably together with other, inert, excipients, is mixed and granulated by roller compaction. The granules obtained can be screened to remove fines. The granules can optionally be coated with the enteric or non-enteric polymers listed above to achieve customized release profiles. Coated or uncoated granules can be filled into hard gelatin capsules or further processed into tablets.

In another preferred embodiment, the drug and permeability enhancing agent(s), with or without polymers that will form complexes with the active agent, and preferably other, inert, excipients, are mixed and granulated using a high-shear granulator. A binder solution or water (if the binder is incorporated as a dry excipient) is used as the granulating fluid. The resulting wet mass is extruded using an extruder device. The thread-like extrudates are then spheronized using a marumerizer (spheronizer). The resulting pellets are dried in an oven or a fluid bed processor. The granules may or may not be coated with the non-enteric or enteric polymers. The coated or uncoated granules may be filled into capsules, or processed into tablets.

The ratio of the active drug to the permeability enhancing excipient can vary from between about 1:1 to about 1:10. The preferred ratio is 1:5.

The amount of active drug in a formulation is dictated by the desired dose of the therapeutic agent for its intended application. For example, a trospium chloride formulation is prepared to provide 10 mg to 80 mg of the drug, depending on the type of formulation and dosage regimen. The amount of the permeability enhancing excipient can be varied depending on the type of permeability enhancer used. For organic acids, drug to permeability enhancing ratio of 1:5 to 1:100 can be used. When organic acids are mixed with complexing polymers, the ratio of organic acid to complexing polymer can be anywhere from about 1:1 to about 9:1.

A pharmaceutical formulation for the delivery of trospium chloride for the effective treatment of urinary frequency, urgency, nocturia, and urge-incontinence associated with detrusor instability, urge syndrome, and/or detrusor hyperreflexia in a human patient comprising a sustained release composition that provides a sustained release of trospium chloride upon oral administration to said patient; and one or more organic acids with a trospium chloride to organic acid(s) ratio of ratio of 1:5 to 1:100; wherein the pharmaceutical formulation is sufficient to maintain an effective level of trospium chloride in the patient over the course of up to 24 hours with or without further administration of trospium chloride. The total dosage of trospium chloride may be about 20 mg to 70 mg producing in a human patient a plasma concentration versus time curve having an area under the curve of about 30,000 pg/ml*hr to about 80,000 pg/ml*hr. The plasma concentration may have a maximum concentration of about 1.5 ng/ml to about 6.0 ng/ml. The plasma concentration may have a minimum concentration of about 0.5 ng/ml to about 1.5 ng/ml. The maximum concentration of value of the said plasma concentration curve may be reached in about 3 to about 24 hours after oral administration.

A pharmaceutical formulation for the delivery of trospium chloride for the effective treatment of urinary frequency, urgency, nocturia, and urge-incontinence associated with detrusor instability, urge syndrome, and/or detrusor hyperreflexia in a human patient comprising a immediate release composition that provides a immediate release of trospium chloride upon oral administration to said patient; and one or more organic acids with a trospium chloride to organic acid(s) ratio of ratio of 1:5 to 1:100; wherein the pharmaceutical formulation is sufficient to maintain an effective level of trospium chloride in the patient over the course of at least to 10 hours without further administration of trospium chloride. The total dosage of trospium chloride per day may be about 30 mg to 80 mg producing in a human patient a plasma concentration versus time curve having an area under the curve of about 30,000 pg/ml*hr to about 80,000 pg/ml*hr, the plasma concentration may have a maximum concentration of about 1.5 ng/ml to about 6.0 ng/ml. The plasma concentration may have a minimum concentration of about 0.5 ng/ml to about 1.5 ng/ml. The maximum concentration of value of the said plasma concentration curve may be reached in about 3 to about 24 hours after oral administration.

Protective overcoats and release controlling coatings may also be applied to the compositions of the present invention with materials well known and in manners known in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention now will be described in particularity with the following illustrative examples; however, the scope of the present invention is not intended to be, and shall not be, limited to the exemplified embodiments below.

EXAMPLES

Example 1

Caco-2 Cell Screening of Permeability Enhancing Excipients

Figure 1:
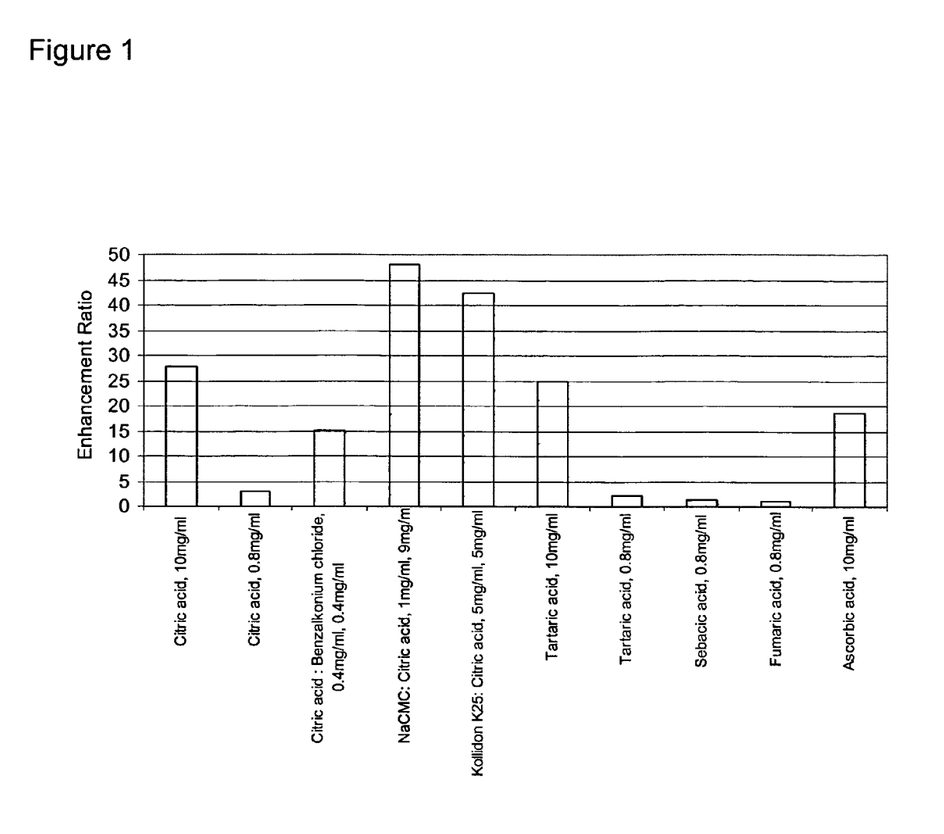
FIG. 1 shows the results of the trospium chloride formulation permeability studies from Example 1 herein.

Up to 1% concentration permeability enhancing excipient solutions were prepared in Hank's Balanced Salt Solution (HBSS), pH 7.4, and agitated overnight. The solutions were filtered using 0.45 mm Teflon Acrodisc filters. A stock solution of trospium chloride (16 mg/ml) was prepared in HBSS, diluted to 160 ug/ml in to the excipient solutions and agitated overnight. Caco-2 cell line permeability studies were conducted in triplicate. The integrity of the Caco-2 monolayer was monitored following the experiments using a cytotoxicity assay. As shown in FIG. 1, several formulations containing organic acids unexpectedly significantly enhanced the permeability of trospium.

Example 2

Figure 2:
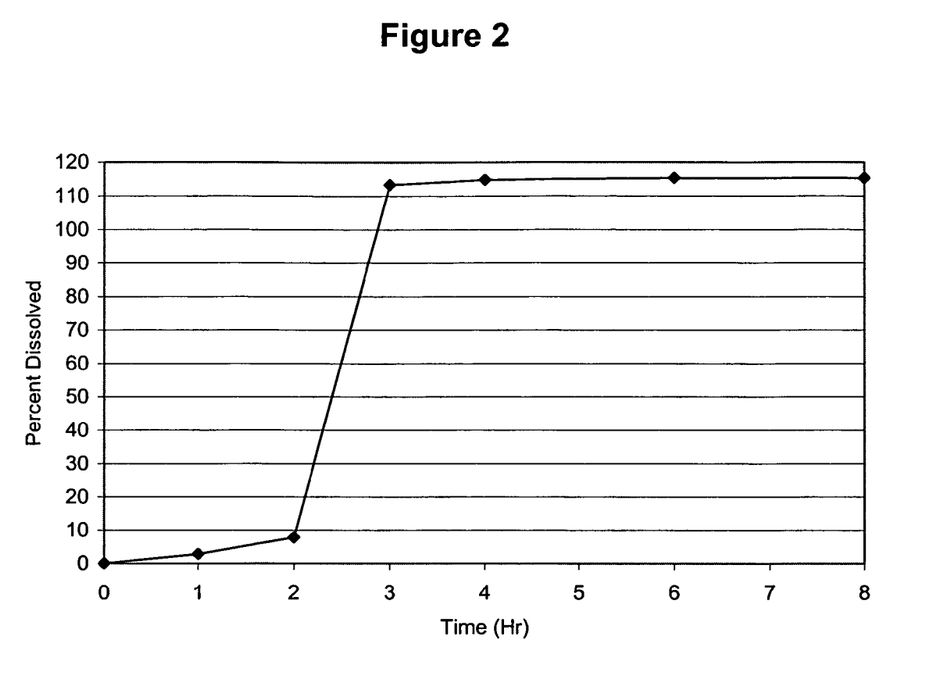
FIG. 2 shows the mean dissolution profile (n=6) for trospium-coated citric acid core coated with Eudragit L30D-55 followed by Opadry White. Dissolution media: 0-2 Hrs: 0.1N HCl, pH 1.1; 2-8 Hrs: phosphate buffer, pH 6.8. USP Apparatus II, 50 RPM at 37° C.

Preparation of Formulations Containing Drug(s) and Enhancing Excipients and the Release Patterns of Drugs and the Enhancer Excipients in Dissolution Media Irregular citric acid granules purchased from a commercial supplier were coated with trospium in a drug to citric acid ratio of 1:5 in a fluid bed coater granulator. First, the irregularly shaped citric acid granules were coated with Eudragit®L30D-55 to a weight gain of 5% followed by an Opadry®white coating to a weight gain of 2%. The granules obtained were then coated with trospium chloride from a trospium chloride (17.7%) solution containing HPMC E5 (1.15%) as a binder. These granules were then coated with Eudragit®L30D55 followed by Opadry® White to weight gains of 40% and 2%, respectively. These granules maintained their irregular shape after the last coating was applied. FIG. 2 provides the mean dissolution profile obtained in dilute HCl, pH 1.1 for the first 2 hours followed by phosphate buffer (pH 6.8).

Example 3

Figure 3:
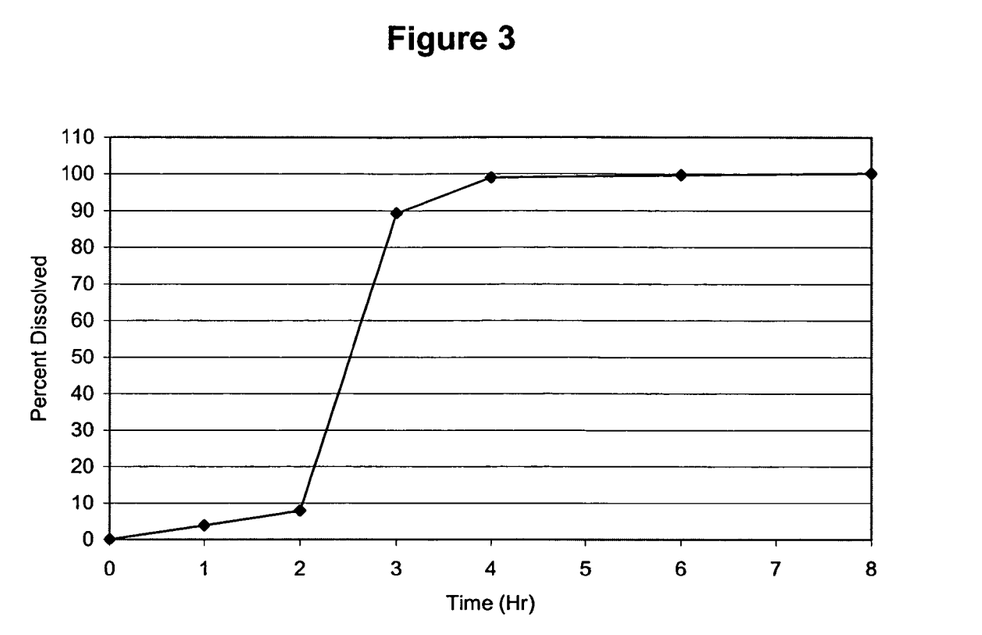
FIG. 3 shows the mean dissolution profile (n=6) for trospium-coated citric acid core coated with Eudragit FS30D followed by Opadry white. Dissolution media: 0-2 Hrs: 0.1N HCl, pH 1.1; 2-8 Hrs: phosphate buffer, pH 7.5. USP Apparatus II, 50 RPM at 37° C.

Trospium-coated citric acid granules were manufactured in the same way as in Example 2. These granules were then coated with Eudragit®FS30D followed by Opadry® white to weight gains of 40% and 2%, respectively. FIG. 3 provides the mean dissolution profile.

Example 4

Separate Active Pellet and Enhancer Pellet Coated with Enteric Polymer to Weight Gains of 40%

Figure 4:
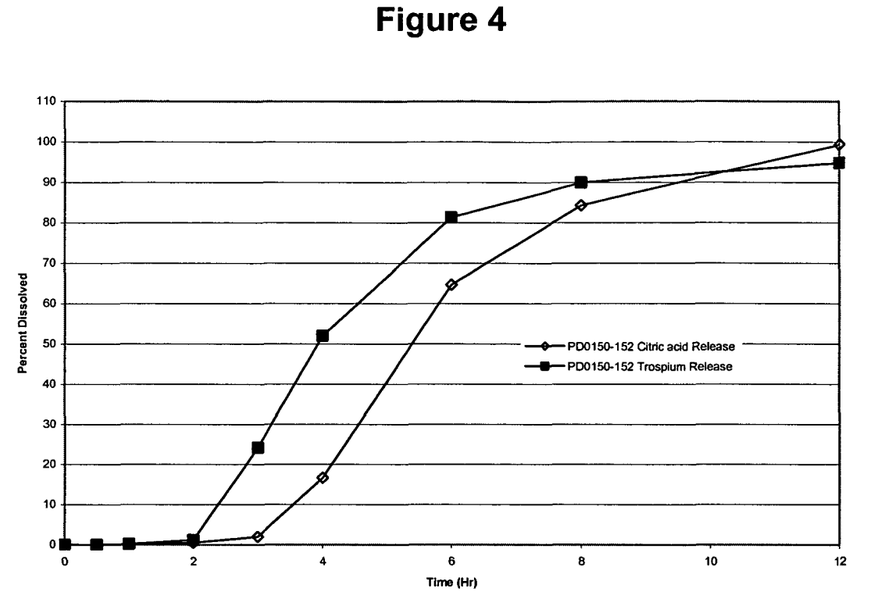
FIG. 4 shows the mean dissolution profile (n=6) for trospium and citric acid from a capsule containing citric acid and trospium pellets coated separately and combined in capsules. Dissolution media: 0-2 Hrs: 0.1N HCl, pH 1.1; 2-8 Hrs: phosphate buffer, pH 7.5. USP Apparatus II, 50 RPM at 37° C.

Citric acid granules and active pellets (trospium-layered sugar spheres) were coated separately with Eudragit®L30D-55L followed by Opadry to weight gains of 40%, and 2%, respectively. Trospium layered sugar spheres (active pellets) are made by coating commercially obtained sugar spheres with trospium chloride solution in a Glatt's fluid bed processor. Coated active and enhancer pellets were combined in a capsule and examined for dissolution of both citric acid and trospium. FIG. 4 shows the mean dissolution profiles for citric acid and trospium.

What is claimed is:

1. A solid oral pharmaceutical dosage form with enhanced gastrointestinal permeability, comprising two separate solid components: (a) a therapeutically effective amount of a quarternary ammonium salt compound, and (b) a permeability enhancing amount of a granulated organic acid.

2. The dosage form of claim 1, wherein the organic acid is a short chain organic acid.

3. The dosage form of claim 2, wherein the short chain organic acid is citric acid.

4. The dosage form of claim 1, wherein the quaternary ammonium salt compound is clidinium, glycopyrrolate, propantheline, or trospium.

5. The dosage form of claim 4, wherein the quaternary ammonium salt compound is trospium chloride.

6. The dosage form of claim 1, wherein the quaternary ammonium salt is combined with at least one electronegatively charged polymer.

7. The dosage form of claim 6, wherein the at least one polymer is selected from cellulosic polymers, alginates, gums, polyacrylic acid derivatives, povidone and its derivatives, polyethylene oxides, or polyvinylalcohol.

8. The dosage form of claim 7, wherein the at least one polymer is selected from guar gum, xanthan gum, carbomers, carageenan, or crospovidone.

9. The dosage form of claim 7, wherein the at least one polymer is selected from hydroxypropylmethylcellulose (HPMC), hydroxypropylcellulose (HPC), hydroxyethylcellulose (HEC), methylcellulose (MC), powdered cellulose, cellulose acetate, sodium carboxymethylcellulose, calcium salt of carboxymethylcellulose, or ethylcellulose.

10. The dosage form of claim 9, wherein at least one of the polymers is HPMC.

11. The dosage form of claim 1 that comprises said granular permeability enhancing agent surrounded by a layer of the quaternary ammonium salt compound.

12. The dosage form of claim 1, wherein component (a) comprises a granulated quaternary ammonium salt compound.

13. The dosage form of claim 12, wherein said dosage form is a capsule or a tablet.

14. An oral pharmaceutical dosage form with enhanced gastrointestinal permeability comprising a multilayered granule comprising a core consisting essentially of a granule of organic acid, and at least one layer comprising a therapeutically effective amount of a quaternary ammonium salt compound surrounding said core.

15. The dosage form of claim 14, wherein said multilayered granule additionally comprises at least one layer of a protective polymer immediately surrounding the core.

16. The dosage form of claim 14, wherein said granule is additionally coated with at least one release-modifying polymer.

17. The dosage form of claim 16, wherein said polymer is an enteric polymer selected from a group consisting of cellulose acetate phthalate, cellulose acetate trimellitate, hydroxypropyl methylcellulose phthalate, polyvinyl acetate phthalate, carboxymethylethylcellulose, and co-polymerized methacrylic acid/methacrylic acid methyl esters.

18. The dosage form of claim 16, wherein said polymer is a non-enteric polymer selected from a group consisting of cellulose acetate, cellulose acetate butyrate, cellulose acetate propionate, ethyl cellulose, fatty acids and their esters, waxes, zein, and aqueous polymer dispersions.

19. The dosage form of claim 6, wherein said polymer forms a complex with the quaternary ammonium compound salt.

20. An oral pharmaceutical dosage form with enhanced gastrointestinal permeability comprising a multilayered granule comprising a core comprising a therapeutically effective amount of a quaternary ammonium salt compound, wherein the core is coated by at least one layer consisting essentially of a permeability enhancing amount of a granulated organic acid.

21. The dosage form of claim 20, wherein said multilayered granule additionally comprises at least one layer of a protective polymer immediately surrounding the core.

22. The dosage form of claim 21, wherein said multilayered granule is additionally coated with at least one release-modifying polymer.

23. An oral pharmaceutical dosage form with enhanced gastrointestinal permeability comprising, a permeability enhancer and a quaternary ammonium salt, wherein the permeability enhancer is contained in coated granules and the quaternary ammonium salt is contained in pellets that are separate from the coated granules.

24. The dosage form of claim 23, wherein the permeability enhancer is a short chain organic acid.

25. The dosage form of claim 24, wherein said organic acid is a citric acid.

26. The dosage form of claim 23, wherein said quaternary ammonium salt compound is trospium.

27. The dosage form of claim 23, wherein the granules and pellets additionally comprise a coating of at least one release-modifying polymer.

28. An oral pharmaceutical dosage form with enhanced gastrointestinal permeability comprising from 10 mg to 80 mg of trospium chloride; a permeability enhancing amount of a granulated short chain organic acid, and at least one electronegatively charged polymer.

29. The dosage form of claim 28, wherein said electronegative polymer is selected from the group consisting of cellulosic polymers, aliginates, gums, polyacrylic acid derivatives, povidone and its derivatives, polyethylene oxides, and polyvinylalcohol.

30. A dosage form of claim 20 wherein said organic acid is a short chain organic acid.

\* \* \* \* \*